(12) United States Patent
van der Maas et al.

(10) Patent No.: US 9,715,673 B2
(45) Date of Patent: Jul. 25, 2017

(54) SYSTEM AND METHOD FOR MANAGING REPLACEMENT OF CONSUMABLES INCLUDING RECYCLABLE GAS PURIFIERS

(75) Inventors: Adriaan Frans van der Maas, Middelburg (NL); Martinus van der Maas, Middelburg (NL); Marinus Frans van der Maas, Middelburg (NL)

(73) Assignee: SCIENTIFIC GLASS TECHNOLOGY SINGAPORE PTE LTD., Singapore (SG)

( * ) Notice: Subject to any disclaimer, the term of this patent is extended or adjusted under 35 U.S.C. 154(b) by 624 days.

(21) Appl. No.: 14/234,002

(22) PCT Filed: Jul. 5, 2012

(86) PCT No.: PCT/NL2012/050477
§ 371 (c)(1),
(2), (4) Date: Apr. 9, 2014

(87) PCT Pub. No.: WO2013/015683
PCT Pub. Date: Jan. 31, 2013

(65) Prior Publication Data
US 2014/0304125 A1 Oct. 9, 2014

(30) Foreign Application Priority Data

Jul. 22, 2011 (SG) .................................. 201105314
Sep. 19, 2011 (EP) ..................................... 11181740

(51) Int. Cl.
*G06Q 10/08* (2012.01)
*G06Q 10/00* (2012.01)
*G06Q 10/06* (2012.01)

(52) U.S. Cl.
CPC ........... *G06Q 10/087* (2013.01); *G06Q 10/06* (2013.01); *G06Q 10/20* (2013.01); *G06Q 10/30* (2013.01); *Y02W 90/20* (2015.05)

(58) Field of Classification Search
None
See application file for complete search history.

(56) References Cited

U.S. PATENT DOCUMENTS

| 5,496,393 | A | * | 3/1996 | Otsuka ................... B01D 46/46 422/119 |
| 5,674,381 | A | | 10/1997 | Den Dekker |

(Continued)

FOREIGN PATENT DOCUMENTS

| EP | 0759485 | 2/1997 |
| EP | 1 942 454 | 7/2008 |

(Continued)

*Primary Examiner* — Ryan Zeender
*Assistant Examiner* — Denisse Ortiz Roman
(74) *Attorney, Agent, or Firm* — Preti Flaherty Beliveau & Pachios

(57) ABSTRACT

A system and a method for managing replacement of consumables, the system including an installed base of equipment assemblies, an installed base of consumables, the consumables including recyclable gas purifiers having a limited lifetime and being used in combination with a said equipment assembly. The system includes a server for registering the consumables and having a module for calculating a replacement advice with respect to the consumable that has been registered in the server. A web portal provides a provider or an end user access to the server via the internet. Various data relating to the end user, its equipment assemblies and its consumables may be inputted via the web portal and the replacement advice that is associated with the registered consumables may be outputted via the web portal.

15 Claims, 6 Drawing Sheets

(56) References Cited

U.S. PATENT DOCUMENTS

| | | |
|---|---|---|
| 6,490,543 B1 | 12/2002 | Jaw |
| 2009/0132321 A1 | 5/2009 | Kamisuwa et al. |
| 2009/0222427 A1* | 9/2009 | Malkowicz ....... G06F 17/30551 |
| 2009/0265118 A1 | 10/2009 | Guenther et al. |

FOREIGN PATENT DOCUMENTS

| | | |
|---|---|---|
| FR | 2898964 | 9/2007 |
| WO | WO 01/61514 | 8/2001 |

* cited by examiner

FIG. 3

SYSTEM AND METHOD FOR MANAGING REPLACEMENT OF CONSUMABLES INCLUDING RECYCLABLE GAS PURIFIERS

FIELD

The invention relates to system for the replacement of consumables having a limited lifetime including gas purifiers that can be recycled.

BACKGROUND

WO01/61514 discloses a process monitoring system for lithography lasers. A number of lithograph lasers at a plant is connected via terminal servers to a central control server. The central control server is connected to the internet and may exchange laser specific information with a server of the lithograph laser manufacturer. The information may prompt the manufacturer to exchange one or more laser modules in the lithograph lasers of the plant.

US2009222427 discloses a tracking system for life limited parts. It is especially directed to monitoring location history of life limited parts that are used in vehicles such as aeroplanes. Apart from tracking information, owner history, remaining life records may be stored in a database.

Gas purifiers for purifying gas, for example carrier gas that is used in a gas chromatograph, a liquid gas chromatograph, a spectrometer or a mass-spectrometer, are known from EP-0 606 960 and EP-1 479 430. No central monitoring systems are available for gas purifiers of such type. The gas purifiers are consumables that are mounted in an equipment assembly, for example, a gas chromatograph equipment assembly, a liquid chromatograph equipment assembly, a spectrometer equipment assembly or a mass-spectrometer equipment assembly. The equipment assembly includes a gas system with a gas source and gas channel that includes gas pipes and that connects the gas source with the gas chromatograph, the liquid chromatograph, the spectrometer or the mass spectrometer. The gas source may be a gas bottle containing carrier gas with certain purity or a gas generator or a liquid gas tank. Generally, a quick change gas purifier base is part of the gas channel. A gas purifier can be mounted by hand on the gas purifier base via a quick change coupling. The known gas purifiers include a purifier material housing in which purifier material is stored and via which the gas flows when the gas purifier is mounted on the base. In order to make the user aware of a limited remaining life time of the gas purifier, generally, the purifier material housing is transparent and at a downstream end is partly filled with indicator material that discolours when the purifier material is saturated and not anymore able to purify the gas flowing through the purifier material. Discolouring indicator material serves as a signal for the end user that the gas purifier should be replaced in order to prevent contamination of the downstream gas channel and apparatus. The purifier material housing is preferably manufactured from glass in order to prevent contamination of the gas flowing through the purifier material housing. In view of the high pressure that may prevail in the purifier material housing, the known purifiers having a purifier material housing that is manufactured from glass are encased by a transparent guard that is made of plastic.

SUMMARY OF THE INVENTION

The inventor has established that, in practice, the sensitivity of the indicator material is in some situations too low to protect the downstream system from contamination with non-purified gas. In such cases, the discolouration of the indicator material is too slow and contaminated gas may exit the gas purifier before the end user may be able to see discolouration of the indicator material. This is especially relevant when the downstream apparatus is very sensitive. Apart from the above, the use of indicator material may be undesired, for example, from an environmental point of view. When the gas purifier has no indicator, the user has no clue when breakthrough of non-purified gas through the filter material occurs. The present invention is directed at solving or alleviating the above problems.

To that end the invention provides a system for managing replacement of consumables, the system including:
- an installed base of equipment assemblies, each equipment assembly including at least one of a gas chromatograph, a liquid chromatograph, a spectrometer and a mass-spectrometer;
- an installed base of consumables, each consumable having a limited lifetime and being used in combination with a said equipment assembly, the installed base of consumables including gas purifiers that are recyclable;
- a server for registering the consumables, the server including:
    - a database for storing various data about the consumables that are used in combination with the installed base of equipment assemblies; and
    - a module for calculating a replacement advice with respect to the consumable that has been registered in the server;
- a web portal configured to give an end user or a provider, such as a manufacturer, a channel partner, a distributor or a service agent of the consumable, access to the server, the web portal being accessible via the internet;
- the web portal being configured for inputting at least the following data:
    - data identifying the end user;
    - a serial number of the consumable that is registered in the server;
    - a date of installation of the consumable in the equipment assembly;
    - a type of the equipment assembly in which the consumable is installed; and
- the web portal being configured to output at least the replacement advice that is associated with the registered consumable of a said end user.

The invention also provides a method for managing replacement of consumables having a limited lifetime, the method including:
- providing a system according to any of the preceding claims;
- inputting via the web portal at least the following data:
    - data identifying the end user;
    - a serial number of the consumable that is registered in the server;
    - a date of installation of the consumable in the equipment assembly;
    - a type of the equipment assembly in which the consumable is installed;
- outputting via the web portal at least the replacement advice that is associated with the registered consumable of a said end user.

By virtue of the system according to claim 1 and the method according to claim 7, the end user is provided with a virtual indicator that is more sensitive than the discolouring indicator material that has been described in the background section. With the system according to the invention it is even possible to use gas purifiers that do not include a discolouring indicator material. As a consequence, the relative expensive transparent purifier material housing may even be dispensed with and be replaced by a non-transparent purifier material housing. As a further consequence, the transparent guard that forms an encasing for the transparent purifier material housing may also be dispensed with. The gas purifier that can be applied in a system according to the invention may be simplified in that the purifier material is stored in a metal purifier material housing. Metal is very suitable to resist high gas pressures. By virtue of the system according to the invention, the end user may be provided with a supply of gas to his equipment of which the purity is guaranteed and that with minimized burdening of the environment. The minimized burdening of the environment may be obtained by the fact that indicator material may be dispensed with and may be promoted by giving end users an incentive to register their consumables and to return their consumables to their provider for recycling. The returning of the consumables to the provider may be done at the right time. A replacement of the consumable that is too late may lead to contamination of the downstream gas system. On the other hand, a replacement that is too early leads to an unnecessary environmental burden in view of the recycling that takes place too soon.

In an embodiment, at least one

Further embodiments are described in the dependent claims and will be further elucidated with reference to an example that is shown in the figure.

BRIEF DESCRIPTION OF THE DRAWINGS

FIG. 3 shows a second example of a web page of an embodiment of a web portal;

DETAILED DESCRIPTION

Figure 1:
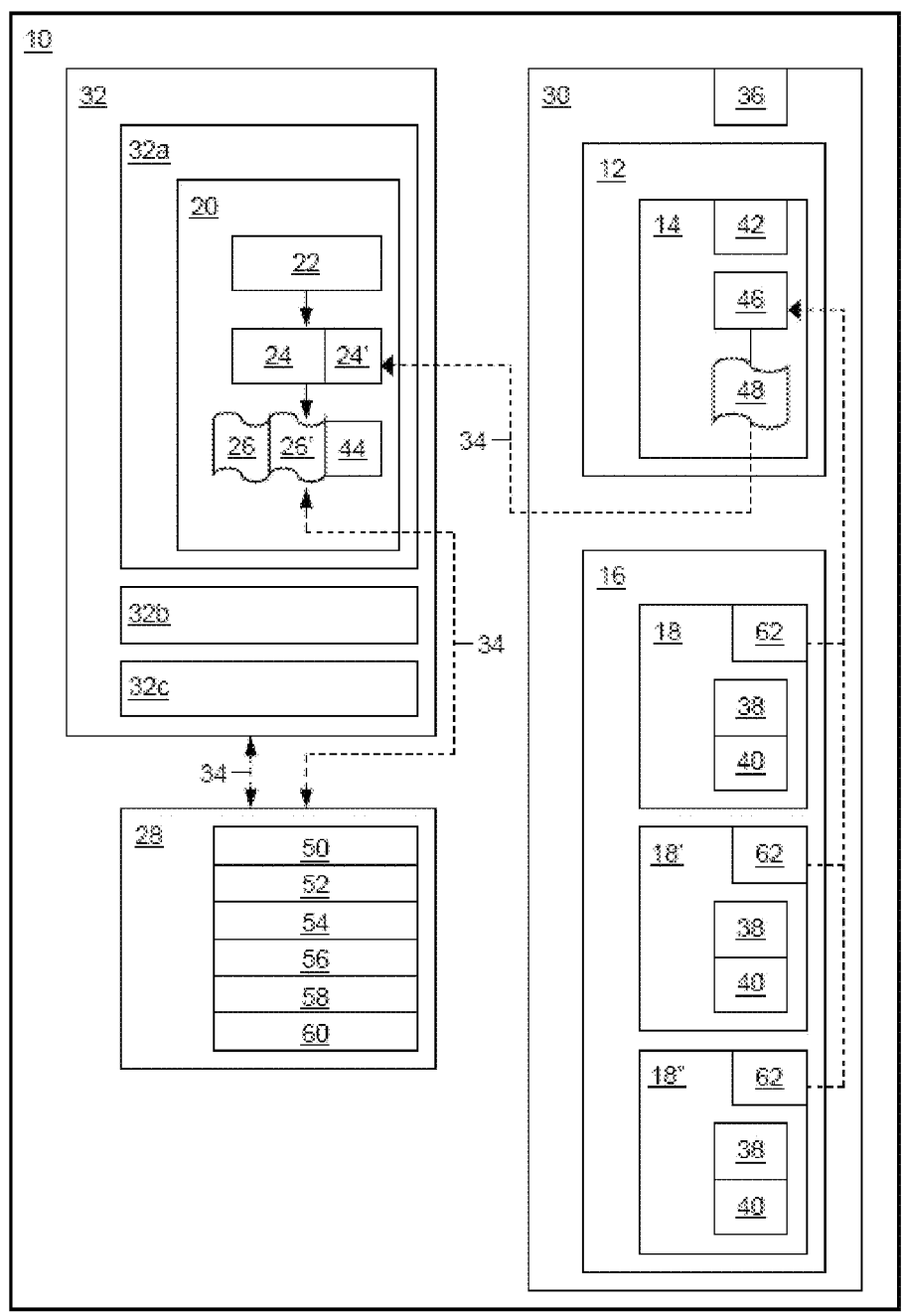
FIG. 1 shows a schematic embodiment of the a system for managing replacement of consumables.

FIG. 1 shows an example of an embodiment of a system for managing replacement of consumables. The system 10 includes an installed base 12 of equipment assemblies 14. Each equipment assembly 14 includes at least one of a gas chromatograph, a liquid chromatograph, a spectrometer and a mass-spectrometer. The system 10 also includes an installed base 16 of consumables 18. Each consumable 18 has a limited lifetime and is used in combination with a said equipment assembly 14. The installed base 16 of consumables 18 includes gas purifiers 18' that are recyclable. Additionally, the consumables 18 may also include chromatography columns 18" and other types of consumables that may be used in an equipment assembly 14. The system 10 includes a server 20 for registering the consumables 18. The server 20 includes a database 22 for storing various data about the consumables 18 that are used in combination with the installed base 12 of equipment assemblies 14. The server 20 also includes a module 24 for calculating a replacement advice 26 with respect to the consumable 18 that has been registered in the server 20. The system also includes a web portal 28 configured to give an end user 30 or a provider 32, such as a manufacturer 32a, a channel partner 32b, a distributor or a service agent 32c of the consumable 18, access to the server 20. The web portal 28 is accessible via the internet 34. The web portal 28 is configured for inputting at least the following data:

data 36 identifying the end user 30;
a serial number 38 of the consumable 18 that is registered in the server 20;
a date of installation 40 of the consumable in the equipment assembly 14;
a type 42 of the equipment assembly 14 in which the consumable 18 is installed.

In a further embodiment, the web portal 28 may also be configured to enter at least one of the following type of data:

the type of gas that is used in the system;
the type of consumable that is used in the system;
the type of service contract the end user has;
the type of "Standard of Operation" (S.O.P.) the end user applies;
the type of gas chromatography column that is used.

Additionally, the web portal 28 is configured to output at least the replacement advice 26 that is associated with the registered consumable 18 of a said end user 30.

With such a system 10, the end user 30 is provided with a virtual indicator of the lifetime of its consumables 18. The system 10 even provides the possibility to use gas purifiers 18' that do not include an indicator material. Thus, the environmental burden may be minimized as well as the costs for the gas purifier 18'. Additionally, the end user may be stimulated by discounts or bonuses to return their consumables 18 to the manufacturer.

The output of the replacement advice 26 may also be executed via SMS, APPS as well as social media platforms such as twitter and facebook.

In an embodiment channel partners 32b and/or distributors or service agents 32c may provide discount codes to their end users 30. When an end user inputs a given discount code in the web portal, the system may be configured to give both the end user 30 and the channel partner 32b and/or the distributor or service agent 32c a discount on new consumables that are to be delivered to the end user 30. Thus, use of the system by end users 30 as well as channel partner 32b and distributors or service agents 32c may be promoted.

The system 10 gives all type providers 32 knowledge about the installed base 12 of equipment assemblies 14 and the installed base 16 of consumables 18 at the end users 30 that are associated with them, which is very valuable from a commercial point of view.

Additionally, various requirements that are imposed by the law, for example the REACH requirements (European Community Regulation on chemicals and their safe use (EC 19072006)) or the RoHS Regulation (Directive 2002/95/EC), may be met with the system according to the invention. Indeed, with the system according to the invention it is easy to register what chemical substances (enclosed by the purifiers) are bought, how the substances are recycled, and at which site the chemicals are.

In an embodiment of the system 10, the module 24 for calculating the replacement advice 26 is configured to calculate an advisable renewal date 44 for the consumable 18 and to include that advisable renewal date 44 in the replacement advice 26.

Thus, the replacement advices 26 may be provided in accordance with a Standard Operation Procedure (S.O.P.)

that may be prescribed by the supplier of the consumable or by an independent institute that is responsible for defining Standard Operations Procedures for various analyses that may be standardized. Based on the S.O.P. the amount of gas that is used may be indicative for the number of analyses that have been performed. Thus, a replacement advice 26 including a renewal date 44 to replace a gas purifier 18' or a gas chromatography column 18" may be given that is based on the amount of gas that has been supplied.

In an embodiment of the system 10, the system may also include a servicing advice module 24' that may provide a service advice 26'. The service advice may be given to the end user 30 but may also be given to a provider 32, such as a manufacturer 32a, a channel partner 32b, and/or a distributor or service agent 32c.

In an embodiment of the system 10 a said equipment assembly 14 may include an electronic controller 46 that is connected to the internet 34. The electronic controller 46 may be a computer, a programmable logic controller (PLC) or a dedicated electronic device for controlling the actions to be performed by the equipment assembly 14. The electronic controller 46 may be configured to collect a use indication value 48 that is indicative of one of the following parameters:

the amount of gas that has passed the consumable 18; and
the duration gas has flown through the consumable 18.

The electronic controller 46 may be configured to input the use indication value 48 into the server 20 via the internet connection 34. The module 24 of the server 20 may be configured include the use indication value 48 in its calculation of the replacement advice 26. Thus the actual use of the consumable 18 of a specific end user 30 may be taken into account when calculating the replacement advice 26. This additional functionality provides more accurate replacement advices 26. In this embodiment, the module 24 may be configured to calculate an advisable renewal date 44 that is dependent on the use indication value 48, wherein the accuracy of the advisable renewal date 44 will, as a consequence, be more accurate. As a consequence, the advisable renewal date 44 may be closer to the actual end of lifetime date, thus resulting in an extended lifetime of the consumable 18.

The consumables 18 may be equipped with a transponder 62, for example, an RFID-transponder that may store just an ID-number, including a serial number, or that may also store data about the use of the consumable 18. The transponder 62 exchanges relevant data with the electronic controller 46, that may, in turn exchange the relevant data via the internet connection 34 with the server 20.

In an embodiment of the system 10 the web portal 28 may include pages that are exclusively accessible for the provider 32 and that provide data including at least one of:

the replacement advices 26 relating to the various registered consumables 18 of a said end user 30;
the type equipment assembly 14 or equipment assemblies 14 used by a said end user 30;
a replacement cycle of consumables 18 of a said end user 30; and
a purchase and/or usage history of consumables 18 of a said end user 30.

Such information may help the provider to predict future demand of consumables 18 of the respective end users 30 and may thus help the provider to keep an efficient number of consumables 18 in stock.

In yet another embodiment the web portal 28 may include pages that are exclusively accessible for the end user 30 and that provide data including at least one of the replacement advices 26 relating to the various registered consumables 18 of the end user 30;
a quality certificate 50 of the consumables 18 used by the end user 30.

In another embodiment, the web portal 28 may include pages that are accessible to both end users 30 and providers 32 and that provide data including at least one of:

a training video 52;
a manual 54;
a knowledge base 56;
on-line technical support 58; and
an on-line user forum 60.

In an embodiment, the web portal 28 may include pages that provide validation information of the system 10. Validation of a system 10 and validation information about that validation is in many cases necessary or compulsory to have for the end user in order to be able to prove that the values of his analyses are indeed valid.

In yet another embodiment, the web portal 28 may include pages that provide the service advice 26' that is determined by the service module 24'. This service advice 26' may be directed to the equipment assembly 14, for example, a gas chromatograph equipment assembly, a liquid chromatograph equipment assembly, a spectrometer equipment assembly or a mass-spectrometer equipment assembly. The service information may also be directed to parts of the equipment assembly 14, for example, the gas chromatograph, the liquid chromatograph, the spectrometer, or the mass-spectrometer. But also other parts of the equipment assembly 14, for example, the gas bottle, the gas generator, the pumps, the valves, the restriction, the gas lines, the columns, the liners etc. For example, the timely exchange of gas bottles may be advised by such a service which is of high importance because the purity the gas delivered by gas bottle diminishes when the gas bottle is emptied.

In another embodiment, the web portal 28 may also be used to input data about the types of analyses that are performed by the equipment assembly 14. When, for example, hazardous substances are involved including radioactive substances, it is of the utmost importance that the company that recycles the consumables has the relevant information about these facts. The web portal 28 may be a convenient means to input such data in the database 22 of the server 20.

As stated before, the web portal 28 may provide an on-line user forum 60 that may promote the dissemination of knowledge relating to the optimal use of the consumables.

The invention also provides a method for managing replacement of consumables having a limited lifetime. The method includes providing a system according to the invention. A provider 32 of consumables 18, for example a manufacturer 32a, a channel partner 32b or a distributor or service agent 32c, or alternatively an end user 30 may input via the web portal 28 at least the following data:

data 36 identifying the end user 30;
a serial number 38 of the consumable 18 that is registered in the server 20;
a date 40 of installation of the consumable 18 in the equipment assembly 14;
a type 42 of the equipment assembly 14 in which the consumable 18 is installed.

The method also includes that at least the replacement advice 26 that is associated with the registered consumable 18 of a said end user 30 is outputted via the web portal 28.

In an embodiment, the method may include that the provider 32 sends, triggered by the replacement advice 26 or by an order from the end user 30, a replacement consumable 18 to the end user 30. The end user 30 may send the consumable 18 to be recycled to the provider 32. A schedule of bonuses or discounts may be implemented to encourage end users 30 and channel partner 32b and distributors or service agents 32c to use the system. By virtue of using the system, the end user 30 obtains a guaranteed supply of clean gas to his equipment assemblies 14 with a minimized burden to the environment in view of the fact that the consumables are returned to the manufacturer for recycling or environmental processing of the consumable 18. Additionally, the providers 32 obtain knowledge of the use of the consumables 18 by their clients, thus facilitating a more efficient stock control of the consumables.

Figure 2:
FIG. 2 shows a first example of a web page of an embodiment of a web portal.

FIG. 2 shows an input page of an example of the web portal 28 in which the type of equipment may be selected.

Figure 3:
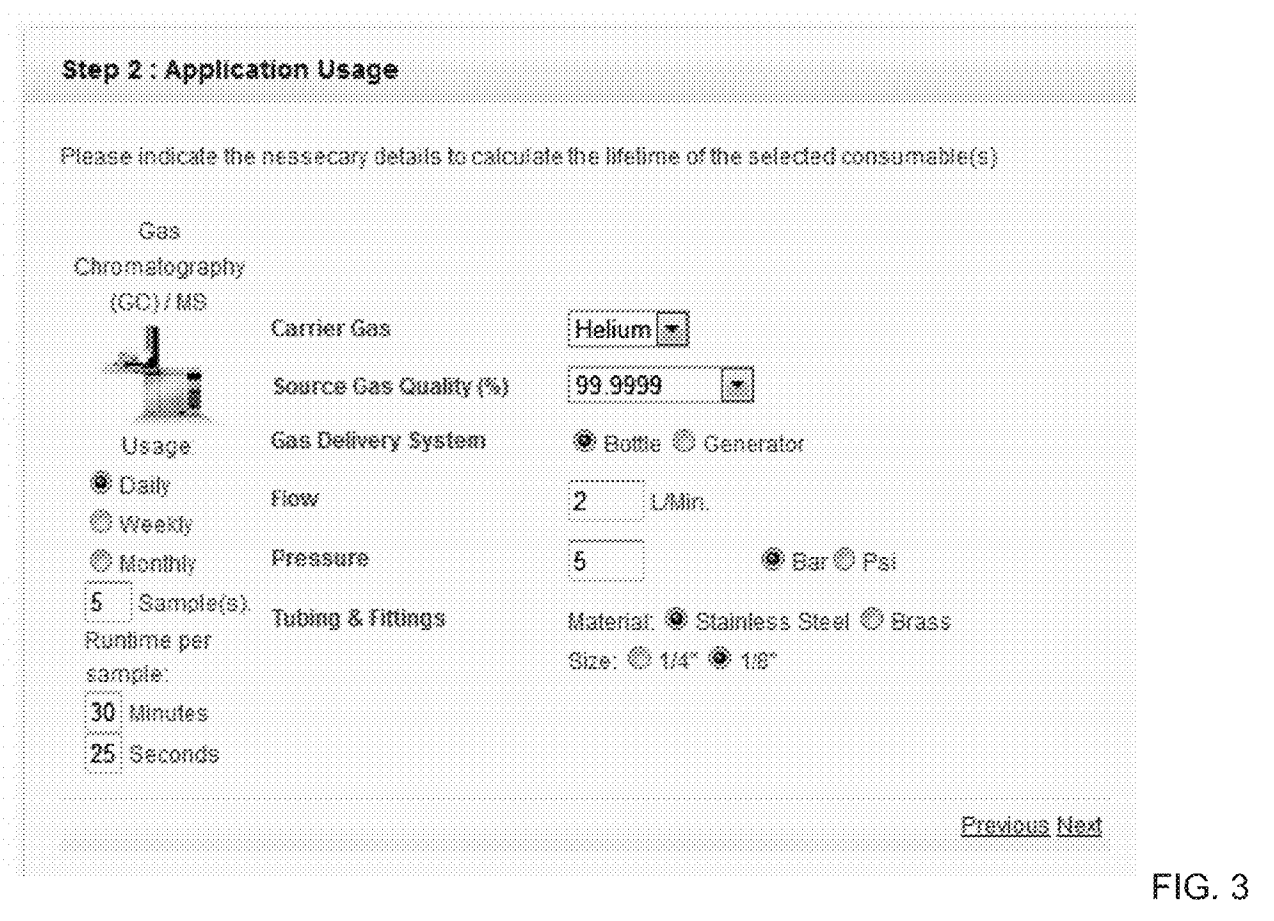

FIG. 3 shows an input page of an example of the web portal 28 in data about the usage of the system may be inputted. For example the frequency of use, the flow of the gas, the pressure of the gas, the number of samples that is measured, the type of tubing, as well as the runtime per sample.

Figure 4:
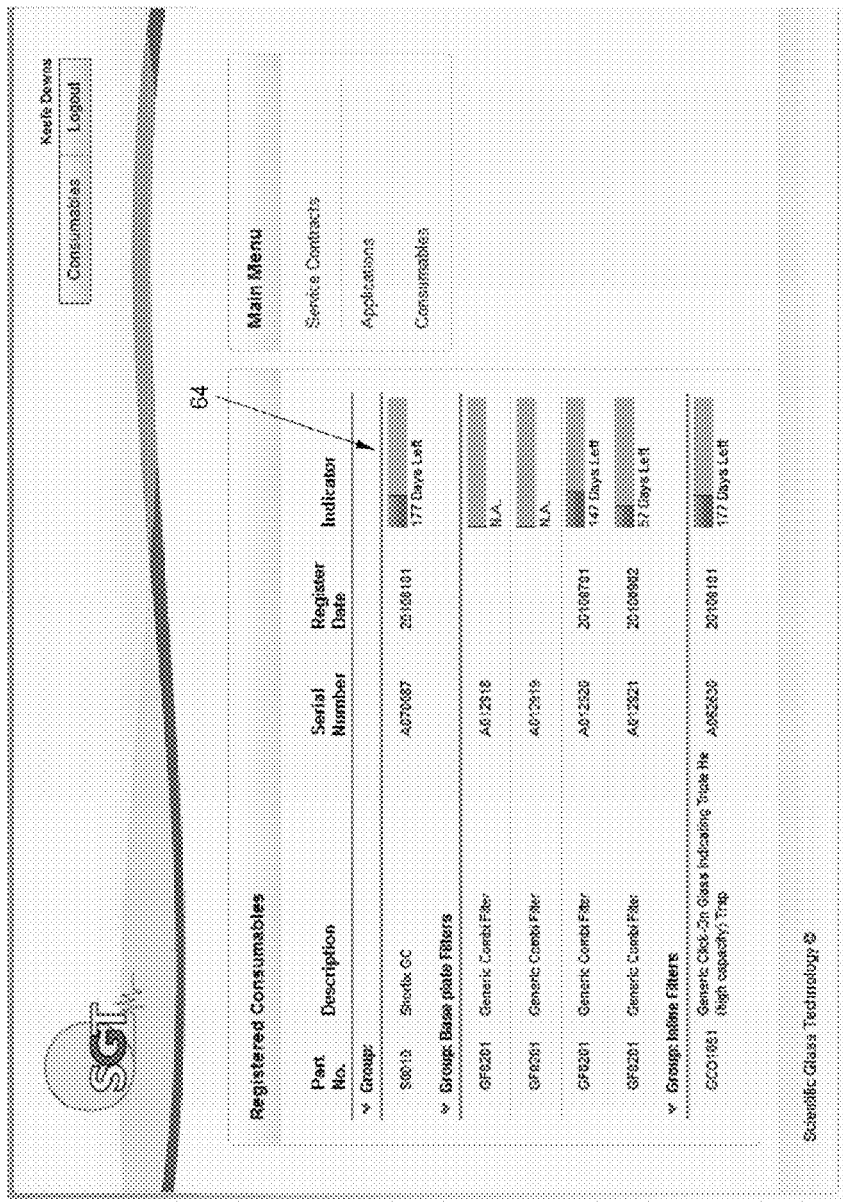
FIG. 4 shows a third example of a web page of an embodiment of a web portal.

FIG. 4 shows an example of an output page of an example of the web portal 28. The output page shows the various types of consumables that are used by the end user 30. A virtual indicator 64, in the form of, for example, a bar of pie graph shows the number of days during which the consumable may be used still. In an embodiment, the output page may also generate a code that may be used to program an electronic programmable signalling device 76, 86 that will be described with reference to FIGS. 5 and 6.

It will be clear that multiple modifications of the various pages of the web portal 28 are possible.

Figure 5:
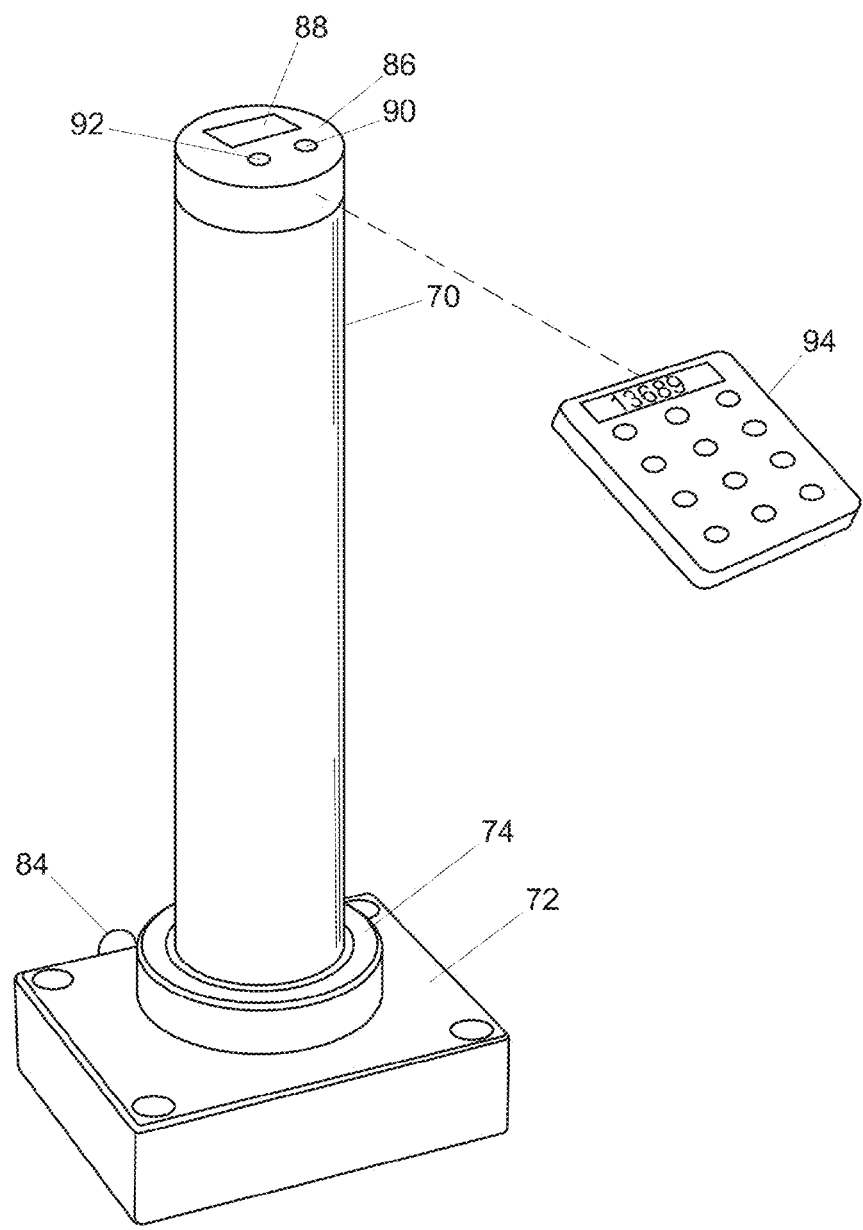
FIG. 5 shows an example of a gas purifier including an electronic programmable signalling device, the gas purifier being mounted on a base plate.

FIG. 5 shows an example of a quick change purifier 70 that is mounted on a base plate 72 of an equipment assembly 14 that normally includes a gas supply system with one or more gas purifiers 70. The base plate 72 is part of the gas supply system and has nipples 84 via which a gas supply line and a gas discharge line of the gas supply system may be connected to the base plate 72. The base plate 74 includes a connection nut 74 that may be tightened and loosened by hand. When a new purifier 70 including filter material has to be mounted on the base plate 74, the nut 74 is unscrewed, the used purifier 70 is removed and a new purifier 70 is mounted on the base plate 72 and fixed by means of the nut 74.

In an embodiment, the gas purifier 70 may include an electronic programmable signalling device 86. In an embodiment, the electronic programmable signalling device 86 may have a display 88 on which a remaining life time or a replacement advice 26 may be displayed. In stead of the display 88 or in addition to the display 88, the signalling device 86 may include coloured light emitting diodes 90, 92, for example a green led 90 indicating that the gas purifier 70 still meets the requirements and a red led 92 indicating that the gas purifier 70 needs to be replaced. In an embodiment, the signalling device 86 may also include a sound signal generator. In that embodiment, the signalling device 86 may produce a sound when it is advisable to replace the gas purifier 70.

Figure 6:
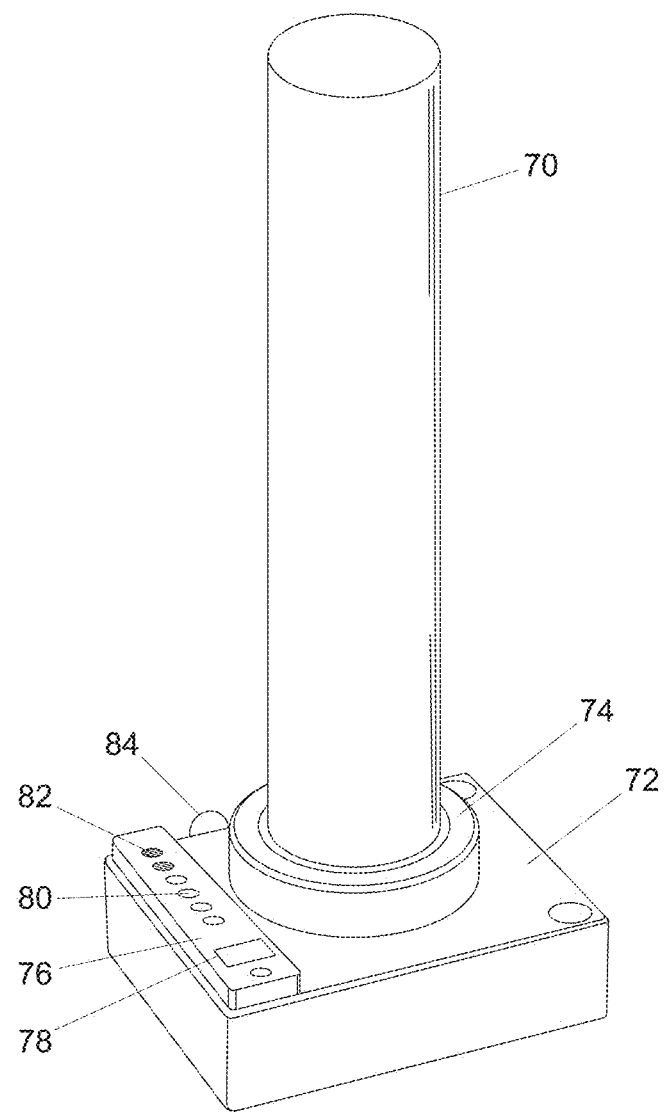
FIG. 6 shows an example of a gas purifier that is mounted on a base plate having an electronic programmable signalling device.

FIG. 6 shows an embodiment in which the base plate 72 is provided with an electronic programmable signalling device 76. The electronic programmable signalling device 76 is associated with the gas purifier 70 that is mounted on the base plate 72. The electronic programmable signalling device 76 may be an integral part of the base plate 72 or may retrofitted on an existing base plate 72. The embodiment shown includes a display 78 and a plurality of leds 80, 82. The led's 80 may have various shades of green and may include one orange led. The led 82 may be red to indicate that replacement of the gas purifier 70 that is mounted on the base plate 72 is imperative.

For both embodiments, the electronic programmable signalling device 76, 86 may be programmed by a supplier of the gas purifier 70 or by a service engineer. After installation of a new gas purifier on a base plate 72, the service engineer will registers the various data about the gas purifier 70 and the equipment assembly 14 in which it is used in the server 20. The module 24 calculates a replacement advice 26. On the basis of this replacement advice 26, the service engineer may program the electronic programmable signalling device 76, 86. Preferably, the programming can exclusively be done by the service engineer or similar person that is associated with the supplier of the gas purifier 70. This can, for example, be effected by using a special programming device 94, such as a code readergenerator that is known from electronic banking to authenticate a user of an electronic banking website. The server 20 may generate a code that includes information that is indicative for a remaining life time in days or months. The code may be inputted into the code readergenerator 94 and the code readergenerator may generate and wirelessly, e.g. via blue tooth, or over a wire provide input to the electronic programmable signalling device 76, 86 to program a remaining life time in the electronic programmable signalling device 76, 86. Once programmed, the electronic programmable signalling device 76, 86 will signal the user of the system when replacement is advisable or needed.

Although illustrative embodiments of the present invention have been described above, in part with reference to the accompanying drawings, it is to be understood that the invention is not limited to these embodiments. Variations to the disclosed embodiments can be understood and effected by those skilled in the art in practicing the claimed invention, from a study of the drawings, the disclosure, and the appended claims. Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, it is noted that particular features, structures, or characteristics of one or more embodiments may be combined in any suitable manner to form new, not explicitly described embodiments.

The invention claimed is:

1. A system for managing replacement of consumables, the system including:
   an installed base of equipment assemblies, each equipment assembly including at least one of a gas chromatograph, a liquid chromatograph, a spectrometer and a mass-spectrometer;
   an installed base of consumables, each consumable having a limited lifetime and being used in combination with a said equipment assembly, the installed base of consumables including gas purifiers that are recyclable;
   a server for registering the consumables, the server including:
      a database for storing various data about the consumables that are used in combination with the installed base of equipment assemblies; and
      a module for calculating a replacement advice with respect to the consumable that has been registered in the server;

a web portal configured to give an end user or a provider, such as a manufacturer, a channel partner, a distributor or a service agent of the consumable, access to the server, the web portal being accessible via the Internet; and at least one electronic programmable signalling device that is associated with a specific consumable of the system, the electronic programmable signalling device including at least one of a display, coloured LEDs and a sound generator to indicate that replacement is required, wherein the electronic programmable signalling device is programmable on the basis of the replacement advice, wherein the web portal is configured for inputting at least the following data:
data identifying the end user;
a serial number of the consumable that is registered in the server;
a date of installation of the consumable in the equipment assembly;
a type of the equipment assembly in which the consumable is installed, and wherein the web portal is configured to output at least the replacement advice that is associated with the registered consumable of a said end user.

2. The system according to claim 1, including:
a programming device that may be connected wirelessly or over the wire with the electronic programmable signalling device and that is configured to be inputted with a code that is generated by the module of the server and that includes information that is indicative for the replacement advice, wherein the programming device sends a programming signal to the electronic programmable signalling device on the basis of which signal the electronic programmable signalling device stores a remaining life time of the associated consumable.

3. The system according to claim 2:
wherein:
the module for calculating the replacement advice is configured to calculate an advisable renewal date for the consumable and to include that advisable renewal date in the replacement advice, further including a servicing advice module configured to provide a service advice;
said equipment assembly thereof including:
an electronic controller that is connected to the internet, the electronic controller being configured to collect a use indication value that is indicative of one of the following parameters:
the amount of gas that has passed the consumable; and
the duration gas has flown through the consumable;
the electronic controller being configured to input the use indication value into the server via the internet; and
the module of the server being configured to include the use indication value in its calculation of the replacement advice;
wherein:
the module is configured to calculate an advisable renewal date that is dependent on the use indication value;
the web portal includes pages that are exclusively accessible for the provider and provides data including at least one of:
the replacement advices relating to the various registered consumables of a said end user;
the type equipment assembly or equipment assemblies used by a said end user;
a replacement cycle of consumables of a said end user; and
a purchase and/or usage history of consumables of a said end user;
the web portal includes pages that are exclusively accessible for the end user and provides data including at least one of:
the replacement advices relating to the various registered consumables of the end user;
a quality certificate of the consumables used by the end user;
the web portal includes pages that are accessible to both end users and providers and that provide data including at least one of:
a training video;
a manual;
a knowledge base;
on-line technical support; and
an on-line user forum;
the web portal includes pages that are accessible to at least the end user of the system and that provide data including validation information of the system;
the web portal includes pages that are accessible to at least the end user of the system and that provide data including the service advice that is determined by the service module, wherein the service advice includes data that is directed to the equipment assembly or parts of the equipment assembly; and
the web portal includes pages that are accessible to the end user and that is configured to inputting data relating to the types of analyses that are performed by the equipment assembly.

4. The system according to claim 1, wherein the module for calculating the replacement advice is configured to calculate an advisable renewal date for the consumable and to include that advisable renewal date in the replacement advice.

5. The system according to claim 1, including:
a servicing advice module configured to provide a service advice.

6. The system according to claim 5, wherein the web portal includes pages that are accessible to at least the end user of the system and that provide data including the service advice that is determined by the service module, wherein the service advice includes data that is directed to the equipment assembly or parts of the equipment assembly.

7. The system according to claim 1, said equipment assembly thereof including:
an electronic controller that is connected to the Internet, the electronic controller being configured to collect a use indication value that is indicative of one of the following parameters:
the amount of gas that has passed the consumable; and
the duration gas has flown through the consumable,
wherein the electronic controller is configured to input the use indication value into the server via the Internet, and
wherein the module of the server is configured to include the use indication value in its calculation of the replacement advice.

8. The system according to claim 7, wherein:
the module for calculating the replacement advice is configured to calculate an advisable renewal date for the consumable and to include that advisable renewal date in the replacement advice; and the module is configured to calculate an advisable renewal date that is dependent on the use indication value.

9. The system according to claim 1, wherein the web portal includes pages that are exclusively accessible for the provider and provides data including at least one of:
the replacement advice relating to the various registered consumables of said end user;
the type equipment assembly or equipment assemblies used by said end user;
a replacement cycle of consumables of said end user; and
a purchase and/or usage history of consumables of said end user.

10. The system according to claim 1, wherein the web portal includes pages that are exclusively accessible for the end user and provides data including at least one of:
the replacement advice relating to the various registered consumables of the end user;
a quality certificate of the consumables used by the end user.

11. The system according to claim 1, wherein the web portal includes pages that are accessible to both end users and providers and that provide data including at least one of:
a training video;
a manual;
a knowledge base;
on-line technical support; and
an on-line user forum.

12. The system according to claim 1, wherein the web portal includes pages that are accessible to at least the end user of the system and that provide data including validation information of the system.

13. The system according to claim 1, wherein the web portal includes pages that are accessible to the end user and that is configured to inputting data relating to the types of analyses that are performed by the equipment assembly.

14. A method for managing replacement of consumables having a limited lifetime, the method including:
providing a system for managing replacement of consumables, the system including:
an installed base of equipment assemblies, each equipment assembly including at least one of a gas chromatograph, a liquid chromatograph, a spectrometer and a mass-spectrometer;
an installed base of consumables, each consumable having a limited lifetime and being used in combination with a said equipment assembly, the installed base of consumables including gas purifiers that are recyclable;
a server for registering the consumables, the server including:
a database for storing various data about the consumables that are used in combination with the installed base of equipment assemblies; and
a module for calculating a replacement advice with respect to the consumable that has been registered in the server;
a web portal configured to give an end user or a provider, such as a manufacturer, a channel partner, a distributor or a service agent of the consumable, access to the server, the web portal being accessible via the Internet; and
at least one electronic programmable signalling device that is associated with a specific consumable of the system, the electronic programmable signalling device including at least one of a display, coloured LEDs and a sound generator to indicate that replacement is required, wherein the electronic programmable signalling device is programmable on the basis of the replacement advice,
wherein the web portal is configured for inputting at least the following data:
data identifying the end user;
a serial number of the consumable that is registered in the server;
a date of installation of the consumable in the equipment assembly;
a type of the equipment assembly in which the consumable is installed, and
wherein the web portal is configured to output at least the replacement advice that is associated with the registered consumable of a said end user;
inputting via the web portal at least the following data:
data identifying the end user;
a serial number of the consumable that is registered in the server;
a date of installation of the consumable in the equipment assembly;
a type of the equipment assembly in which the consumable is installed;
outputting via the web portal at least the replacement advice that is associated with the registered consumable of said end user to the at least one electronic programmable signaling device that is associated with the registered consumable.

15. The method of claim 14, including that:
the provider sends, triggered by the replacement advice or by an order from the end user, a replacement consumable to the end user; and that
the end user sends the consumable to be recycled to the provider.

* * * * *